United States Patent [19]
Girolami

[11] 4,081,242
[45] Mar. 28, 1978

[54] APPARATUS AND METHOD FOR MEASURING THE TIME TAKEN FOR A CHANGE IN VISCOSITY TO OCCUR

[76] Inventor: Antoine Girolami, 57, rue du Coq, 13001 Marseille, France

[21] Appl. No.: 704,650

[22] Filed: Jul. 12, 1976

[30] Foreign Application Priority Data

Jul. 16, 1975 France .................. 75 22641

[51] Int. Cl.² .................. G01N 33/16; G01N 11/10
[52] U.S. Cl. .................. 23/230 R; 23/230 B; 23/259; 23/253 R; 73/54; 73/57; 73/64.1
[58] Field of Search .............. 23/259, 253 R, 230 B, 23/230 R; 73/64.1, 57, 54

[56] References Cited

U.S. PATENT DOCUMENTS

| | | | |
|---|---|---|---|
| 3,375,705 | 4/1968 | Kim | 73/57 |
| 3,707,871 | 1/1973 | Emmet | 73/57 |
| 3,888,113 | 6/1975 | Miranda | 23/259 X |
| 3,967,934 | 7/1976 | Seitz et al. | 73/64.1 X |

*Primary Examiner*—R.E. Serwin
*Attorney, Agent, or Firm*—William Anthony Drucker

[57] ABSTRACT

An apparatus for measuring the time taken for a change to occur in the physical state of a material or medium, such as the time of appearance of a clot in a blood sample, includes a jar whose bottom may serve as a circular track for a ball, a ball able to roll around the track, a support for the jar maintaining the bottom of the jar and track in a plane inclined in relation to the horizontal plane, a means for rotating the support and jar whereby the ball remains at the lowest point of the track when the material is in the liquid state but is carried around the track by the more viscous material when that has changed its state, and a means of detecting the movement of the ball.

6 Claims, 9 Drawing Figures

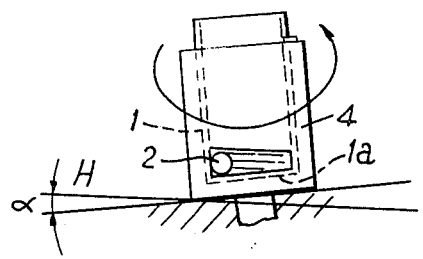
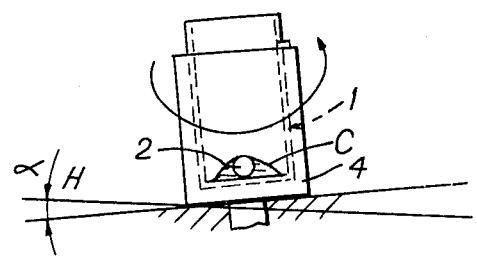
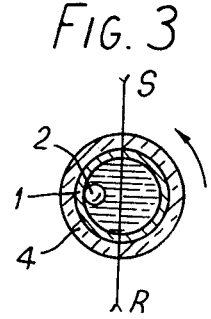
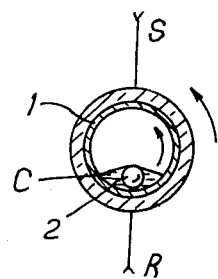
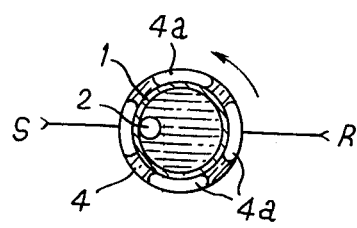
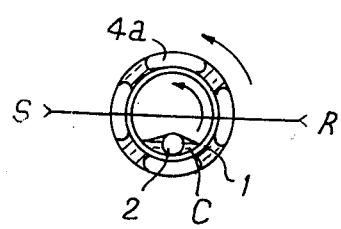
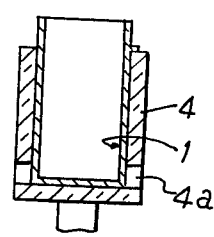

APPARATUS AND METHOD FOR MEASURING THE TIME TAKEN FOR A CHANGE IN VISCOSITY TO OCCUR

This invention relates to an apparatus and a method for measuring the time taken by a change in the physical state of a material or medium. A particularly useful example of application, though in no way limiting the subject-matter of the invention, is the measurement of the time required for a clot to appear in a sample of blood or plasma, treated with a reagent such as thromboplastin or another, i.e. measurement of the coagulation time of blood or blood plasma.

Various devices and methods have already been recommended for measuring the time taken for a clot to form in a blood sample, which makes it possible to determine the appropriate medical treatment in certain diseases.

An apparatus used for this purpose includes a container containing the blood sample, a cylindrical ferromagnetic component positioned inside this container, means of rotating said container and a magnetic field detector positioned outside the container; the magnetic field as well as the weight of the cylindrical ferromagnetic component tending to maintain the latter close to the detector, which makes it possible to record the change occurring in the magnetic circuit when the liquid solidifies and generates mechanical and adhesive forces between said component and the inside wall of the container of sufficient magnitude to overcome the force maintaining the component in the predetermined position; said instrument also including precision timekeeping means to record the signal indicating the end of the change of state time of the blood sample.

This instrument has certain disadvantages due to the fact that a cylindrical ferromagnetic component or magnet is used. It is in particular essential, in this case, to associate a magnetic field detector or transformer with the ferromagnetic component, which necessarily leads to the construction of complex instruments, while other methods of detection (optical, etc.) are excluded, which constitutes a constricting limitation.

Moreover, the use of a ferromagnetic component has a serious disadvantage arising from the fact that when the container is rotated, said component remains in its initial bottom position because of the force of gravity allied to the mutual magnetic attraction between said component and the detector.

In fact blood which has clot-forming deficiencies cannot always produce sufficient adhesive forces between the clot and the smooth inner wall of the container to overcome the above-mentioned forces of gravity and magnetism. In this case, when such clots appear, since the container subsequently continues to rotate, the clot slips in relation to the inner wall, so that said magnet remains close to the detector which therefore does not emit any signal in consequence of the formation of said clot.

In an attempt to overcome this major disadvantage, provision has been made for equipping the inner wall of the container with irregularities, which complicates its manufacture and handling while making cleaning operations difficult, thus increasing the risk of contamination which can have an undesirable effect on the coagulation process.

Moreover, the use of a cylindrical component also gives rise to a serious disadvantage arising from the fact that more often than not it occupies a crosswise position in the container and the non-uniform formation of the clot causes it to be driven irregularly by one of its ends, which disturbs the operation of the magnetic field detector and makes it impossible to replace the latter by an optical detection system.

To overcome this disadvantage, provision has been made to house an axial guide component in the container, which is not very effective and also complicates the manufacture of the apparatus and handling, making cleaning inconvenient and thus increasing the risk of harmful contamination.

Moreover, this cylindrical component, held in an initial position by magnetic attraction, slips on the inner wall of the container generating considerable friction so that it slips in jerks on said wall and this irregular slip may cause untimely operation of the detector.

The apparatus in accordance with this invention overcomes all these disadvantages.

One of the aims of the invention is the construction of an apparatus similar to the kind mentioned above, capable of being fitted with some sort of detection system and wherein the component indicating the change in the state of the blood liquid is naturally suited to occupy the most accurate possible initial position, which enables the detection means to operate perfectly and very accurately, regardless of their nature.

Another aim of the invention is the construction of an apparatus in which said component is always driven regularly as soon as the clot forms, even if the latter does not form evenly.

Another aim of the invention is to obtain virtually no friction between the smooth inner wall of the container and the signalling component when these are in relative motion.

Another aim of the invention is the construction of an apparatus consisting of simply-shaped parts making it possible to clean them easily and safely, without long and difficult handling.

The apparatus for measuring the time taken for a change to occur in the physical state of a material or medium in accordance with the invention comprises at least one jar, the bottom of which is adapted to serve as a circular track for a ball, a support for the positioning of the jar in a position where said circular track is situated on a plane inclined in relation to the horizontal plane, means for rotating said support and the jar, and a ball adapted to be housed in said jar.

These aims and characteristics, and others, will emerge more clearly from the ensuing description and the accompanying drawings wherein:

FIGS. 1 and 2 are simplified views of the apparatus, showing two phases during the application of the method claimed.

FIGS. 3 and 4 are cross-sectional views at ball level, illustrating the operation of the apparatus equipped with a detection system operating by occultation of a light ray or other beam emitted by said system and corresponding, respectively, to FIGS. 1 and 2.

FIGS. 5 and 6 are cross-sectional views at ball level, illustrating the operation of the apparatus equipped, in accordance with another embodiment, with a detection system operating by establishment of a light ray or other continuous beam between the source of radiation and the receiver of said system and corresponding, respectively, to FIGS. 1 and 2.

FIG. 9 is an axial section of the opaque jar support in accordance with FIGS. 5 and 6.

Figure 7:
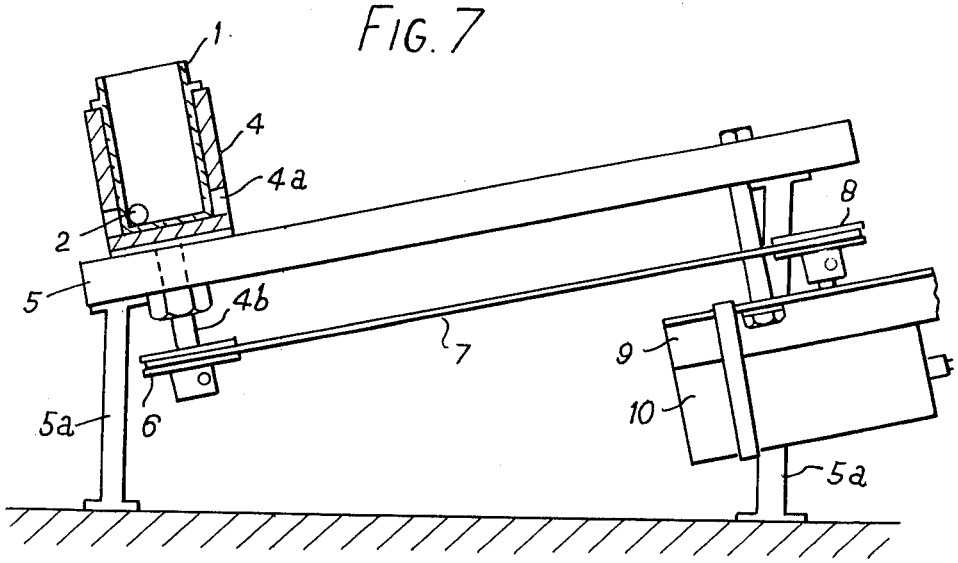
FIG. 7 is a side view, in partial section and of a diagrammatic type, of an elementary construction of the apparatus.

In accordance with the apparatus and method covered by the invention, the medium of which it is wished to measure the time taken by a change of physical state, e.g. a sample of blood, is introduced into a small cylindrical jar 1 capable of being rotated and whose bottom 1a is suitable to serve as a circular track for a ball and position on an inclined plane at an angle $x$ to the horizontal plane H.

In this jar, a ball or spherical unit 2 made of stainless steel, glass, plastic or any other suitable material, is housed.

It will be understood that this ball, submerged in a fluid or slightly viscous medium, remains very accurately in the low position or sinks by gravity to the bottom of the jar when the latter is rotated around its inclined axis (FIGS. 1, 3 and 5).

The reagent or other chemical is introduced in a measured quantity into the jar 1 by means of any suitable device such as an electric pipette, simultaneously controlling the starting of the time measuring instrument such as a chronometer, in accordance with known methods.

In the application more specifically designed to investigate the prothrombin or clot formation time, a measured quantity of, e.g., thromboplastin, is introduced into the jar 1. When a certain time has elapsed after this introduction, the increase in viscosity of the mixture causes the ball 2 to be carried in a circular motion around the inclined axis of the jar.

In the aforesaid application, the ball is carried along as soon as clot C appears and prevents said ball from rolling and it is held in the viscous mass of said clot (FIGS. 2, 4 and 6) which adheres to the smooth inner wall of the jar 1.

The commencement of the circular movement of the ball can be ascertained visually or by means of any suitable detection system. In the first case, the operator will stop the chronometer manually as soon as he sees the ball being carried in a circle, while in the second case, said chronometer will be stopped as soon as the detection system with which it is associated in a known way detects the commencement of the circular travel of said ball.

The time between the introduction of the reagent and the circular motion of the ball is the time taken for the physical state of the medium to change and, in the application mentioned above, the coagulation time for the blood or blood plasma.

In order to increase the accuracy and output of the apparatus, the latter preferably includes a detection system designed to control the stopping of the timing instrument and/or display of the required information, as soon as the change in the physical state of the material or medium under study is ascertained.

This detection system can consist of any known device such as a photo-electric cell or other device operating by breaking or making a continuous ray between the source of radiation energy and the receiver of said system. This system can also operate by detection of the change in an electric or magnetic or electro-magnetic field generated by the ball's movement.

In the first case, the jar 1 is made of a material which is transparent or can be permeated by the light ray or other radiation, such as glass for example, while the ball 2 is made of a material which is opaque or impermeable to said light ray or other radiation. The diagrams in FIGS. 3 and 4 illustrate the working of an apparatus equipped with a detection system operating by occultation of a light beam or other radiation joining the source of radiation S and the receiver R of said system.

In FIG. 3, the ball 2 is in the low position at the bottom of jar 1, and continuity is established between the source of radiation S and the receiver R of the detection system. No pulse reaches the device controlling the timing instrument. In FIG. 4, the ball 2 is trapped in the viscous mass or clot C and is carried in a circular movement. As soon as it begins to travel, it intercepts the light ray or other radiation joining the source of radiation S to the receiver R of the detection system. This occultation causes a pulse to be sent to the device controlling the timing instrument, which stops said instrument.

The detection system can also operate by establishing a light beam or other continuous radiation between the source of radiation S and the receiver R of said system, as shown in FIGS. 5 and 6. In this case, the light beam or other radiation is cut by the presence of the ball between the source of radiation and the receiver of the detection system, when said ball is in the low position at the bottom of the jar (FIG. 5); the device controlling the timing instrument receives no pulse.

As soon as the ball commences its circular travel as a result of the appearance of the clot, the continuity of the light beam or other radiation is established between the source of radiation S and the receiver R (FIG. 6); the establishment of this continuity causing a pulse to be sent to the device for controlling the timing instrument, which stops said instrument.

Figure 8:
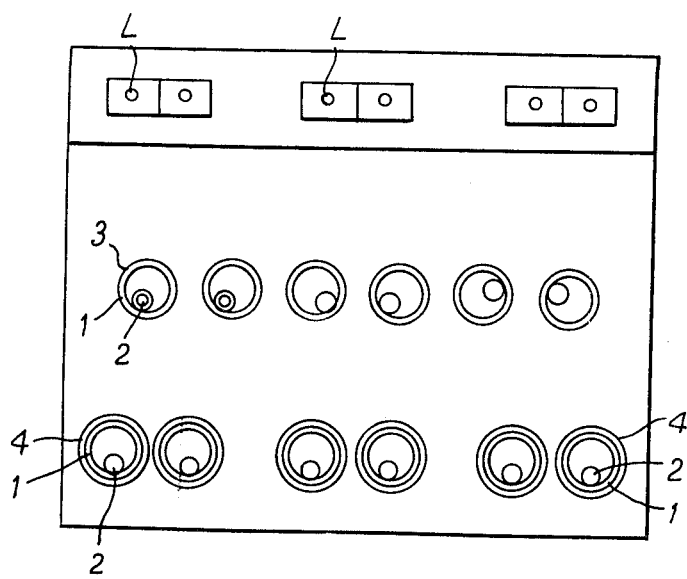
FIG. 8 is a diagrammatic view, from above, of an apparatus making it possible simultaneously to carry out measurements of the time taken by a change in the physical state of several samples of a material or medium.

As is shown diagrammatically in FIG. 8, the apparatus in accordance with the invention can be made with a plurality of jars 1 rotated simultaneously, or in groups of two or more than two, or completely independently, by means of any known drive and coupling means. In this case, the apparatus includes a detection system associated with each jar and each of the detection systems is connected to the device controlling a timing instrument, as well as possibly to a signal such as a pilot-lamp L indicating the end of the measurement operation. Moreover, the apparatus preferably comprises cavities temperature-controlled by means of any known heat regulating device and designed to take a plurality of jars equipped with their balls, in order to maintain said jars and balls at the required temperature.

As indicated above, rotation of jar(s) 1, e.g. at a speed of the order of 1 revolution per second, can be effected in any known way.

In FIG. 7, an example of a simplified arrangement of the apparatus has been shown.

The transparent cylindrical jar 1 with a flat bottom 1a perpendicular to its axis of rotation, is placed in a cylindrical support 4 of complementary size, mounted rotatably around an inclined axis, by means of any suitable bearing, on a base 5 or on the upper surface of the instrument's housing. In this way, the bottom of the jar 1 or the surface of said bottom suitable to serve as a track for the ball 2 is on an inclined plane in relation to the horizontal plane, as indicated before. In view of its spherical shape, the ball is only in point contact with the bottom 1a and the inner side wall of the jar 1.

The bottom of the support 4 is fixed to a rod or axle 4b on which a pulley 6 is keyed, positioned beneath the base 5. On this pulley, the belt 7 winds, which is also mounted on the pulley 8 keyed on the output shaft of a speed reducer 9 coupled to the electric motor 10 of the apparatus.

The inclined mounting of the axis of rotation of the jar support can be obtained by any suitable footing 5a or by any suitable shaping of the housing of the apparatus.

It is easy to understand that it is possible to fit the apparatus with several jar supports which can be driven simultaneously in any known way and, e.g., by means of pulleys at different levels and pulley belts, by an endless screw system, etc. Of course, each jar 1 could be driven independently, just as it is possible to drive said jars in groups of two or more than two, without it being necesssary to describe such arrangements which contain no inventive element.

A construction of this kind makes it possible simultaneously to carry out several measurements of the time taken for the physical state of a material or medium to change, such as measurement of the coagulation time of a certain number of samples of blood or blood plasma.

When the apparatus is equipped with one or several detection systems operating by occultation of a light beam or other radiation, the jar support(s) 4 are made of a material which is transparent or permeable to said light beam or other radiation (glass or transparent plastic, for example).

This is not necessarily the case when the detection system(s) operate by establishment of a light beam or other continuous radiation between their source of radiation and their receiver. In this case, in fact, the support 4 can be made of an opaque material and comprise peripherically, at the base, a plurality of elongated apertures 4a, regularly spaced and diametrically opposite in pairs, as is shown in FIGS. 5, 6 and 9.

Before it is immobilised in the viscous mass C, the ball 2 or the partitions separating the apertures 4a intercept the light beam or other radiation produced by the source of radiation S of the detection system (FIG. 5).

When the ball is carried in a circular movement, the continuity of the light beam or other radiation between the source of radiation S and the receiver R can be established through two diametrically opposite apertures, since at least one of the pairs of apertures will necessarily be exposed, irrespective of the position of the clot and said ball (FIG. 6).

It is recalled, finally, that while reference has been made, in the foregoing exposition, to the particularly useful application to which this patent relates of measuring the coagulation time of blood or blood plasma treated with various reagents (recalcifying solutions, thromboplastic, etc.), the method and apparatus claimed are suitable for measuring the time taken by a change in the physical state of media or materials of widely varying natures (measurement of the polymerisation time of certain resins, for example).

It is also possible, for certain materials or media, to make measurements in the reverse direction, i.e. starting with a thick medium constituting a mass in which a ball has previously been caught, said mass being placed in the rotating jar and fluidising progressively in time, e.g. under the action of a reagent or other chemical.

The end of the measuring operation is then determined by the cessation of the ball's circular travel and its becoming stationary in the low position or dip.

I claim:

1. An apparatus for use in a method of detecting change of viscosity to occur in a medium, comprising:
   (i) a receptacle to contain an amount of the medium, said receptacle including a planar base and a bounding wall upstanding from said base
   (ii) a structure, and means mounting said receptacle on said structure for rotation of said receptacle with respect to said structure about an axis of rotation normal to the plane of said base, said structure and mounting means being such that said planar base lies at an inclination to the horizontal,
   (iii) drive means on said structure coupled to said receptacle for rotating said receptacle with respect to said structure,
   (iv) a ball of greater density than said medium positioned in said receptacle and supported by said planar base and said bounding wall for rolling along said base and wall as the receptacle is rotated.

2. An apparatus, as claimed in claim 1, wherein said receptacle is a cylindrical jar having said planar base and upstanding wall.

3. An apparatus, as claimed in claim 2, wherein said means mounting said receptacle on said structure include a cylindrical support receiving said cylindrical jar.

4. An apparatus, as claimed in claim 1, further comprising means for producing a beam of radiation for passing through said receptacle, and means for detecting said beam of radiation after passing through said receptacle, said receptacle being permeable to said radiation, and said ball being impermeable to said radiation.

5. An apparatus, as claimed in claim 1, wherein said means mounting said receptacle on said structure include a support receiving said receptacle, said support having opposed apertures aligned with the position occupied by the ball in the receptacle when supported by the base and bounding wall of the receptacle, and further comprising means for producing a beam of radiation for passing through said receptacle and the apertures of said support, said receptacle being permeable to said radiation, said support and said ball being impermeable to said radiation, and means for detecting said beam of radiation after passing through said receptacle and the apertures of said support.

6. A method, of detecting a change of viscosity in a medium, which comprises the steps of:
   (i) placing a quantity of medium in a receptacle having a planar base and a bounding wall upstanding from said base
   (ii) placing a ball in said medium in said receptacle
   (iii) rotating said receptacle, containing said medium and said ball, about an axis normal to the plane of said base, said axis being at an inclination to the horizontal, and
   (iv) detecting any change occurring, in either direction, between a first state of viscosity of the medium in which the ball remains substantially in the same position as it is supported by and rolls along said base and bounding wall, and a second state of viscosity of the medium in which the ball is carried by the medium about the axis of rotation of the receptacle.

* * * * *